United States Patent [19]

Knifton

[11] Patent Number: 4,556,734

[45] Date of Patent: Dec. 3, 1985

[54] PROCESS FOR SYNTHESIZING FORMAMIDES FROM SYNTHESIS GAS PLUS AMMONIA

[75] Inventor: John F. Knifton, Austin, Tex.

[73] Assignee: Texaco Inc., White Plains, N.Y.

[21] Appl. No.: 548,900

[22] Filed: Nov. 4, 1983

[51] Int. Cl.[4] ............................................ C07C 102/00
[52] U.S. Cl. ...................................................... 564/132
[58] Field of Search ......................................... 564/132

[56] References Cited

U.S. PATENT DOCUMENTS

| | | | |
|---|---|---|---|
| 3,168,553 | 2/1965 | Slaugh | 564/132 X |
| 3,446,842 | 5/1969 | Nozaki et al. | 564/132 |
| 3,530,182 | 9/1970 | Haynes et al. | 564/132 |
| 3,580,968 | 5/1971 | Kuraishi et al. | 564/132 X |
| 4,094,905 | 6/1978 | Mizuno et al. | 564/132 |
| 4,244,889 | 1/1981 | Bartley et al. | 564/132 |
| 4,269,998 | 5/1981 | Inai | 564/132 |
| 4,331,612 | 5/1982 | Pesa et al. | 564/132 X |

FOREIGN PATENT DOCUMENTS

| | | | |
|---|---|---|---|
| 1902560 | 8/1969 | Fed. Rep. of Germany | 564/132 |
| 371555 | 4/1932 | United Kingdom | 564/132 |

Primary Examiner—Thomas A. Waltz
Attorney, Agent, or Firm—Jack H. Park; Kenneth R. Priem; Cynthia L. Kendrick

[57] ABSTRACT

A process is disclosed for the production of formamides, particularly N,N-dimethylformamide and N-methylformamide, by the reaction of synthesis gas with ammonia in the presence of a catalyst system comprising a ruthenium species coupled with quaternary phosphonium salts. The catalyst system typically produces high yields of formamides, a large percentage of which may comprise N,N-dimethylformamide, N-methylformamide or formamide itself.

13 Claims, No Drawings

PROCESS FOR SYNTHESIZING FORMAMIDES FROM SYNTHESIS GAS PLUS AMMONIA

FIELD OF THE INVENTION

This invention relates to a process for synthesizing formamides, especially N,N-dimethylformamide and N-methylformamide, from synthesis gas, i.e., a mixture of carbon monoxide and hydrogen, plus ammonia in the presence of a catalyst system comprising a ruthenium-containing compound dispersed in a quaternary phosphonium salt, heating the mixture to a temperature of at least 100° C. and a pressure of at least 500 psi until there is substantial formation of the desired formamides and derivatives thereof and separating said formamide product.

BACKGROUND OF THE INVENTION

The preparation of formamide and N-substituted formamides from carbon monoxide and ammonia, primary or secondary amines is known to the art (U.S. Pat. Nos. 1,532,428 and 2,793,211). Widely varying reaction conditions have been reported, as has the use of various catalysts. Many of these processes give acceptable yields but require the carbon monoxide reactant to be free of substantial amounts of carbon dioxide, water (U.S. Pat. No. 2,866,822) and oxygen, (British Patent No. 823,778).

U.S. Pat. No. 3,781,352 discloses a process for producing formamides by mixing together ammonia or amine, carbon monoxide and oxygen in the presence of a catalyst, such as sodium methoxide, at a temperature of from about 20° C. to about 260° C. and at a pressure from about 10 to 200 atmospheres. The advantage of this process is that off-gases from basic oxygen furnaces in, for example, steel making plants can be advantageously used in the manufacture of formamide without first removing the oxygen.

In the preparation of N-alkylformamides, such as N,N-dimethylformamide, it has been the practice for some time to prepare these from the corresponding primary or secondary alkyl amine and carbon monoxide. Sodium in alcohol or sodium methoxide are typical catalysts. In European Patent Application No. 49,581, as well as U.S. Pat. No. 2,866,822, for example, N,N-dimethylformamide is produced from dimethylamine and carbon monoxide with an alkali metal methylate catalyst. Such preparations are often characterized by high pressures, high temperatures and long reaction times. Transition-metal catalysts are now often used to circumvent some of these problems. Kudo, Kiyoshi et al. in Chem. Lett. 1977, p. 1495, employ a palladium chloride catalyst and a base to prepare dimethylformamide from dimethylamine. In U.S. Pat. No. 3,446,842, N,N-dimethylformamide is produced by carbonylating a mixture of ammonia and methylamine in the presence of certain cobalt-containing catalysts. Similarly in German Patent No. 863,800, contacting of trimethylamine and carbon monoxide in the presence of a supported catalyst comprising mixtures of oxides and magnesium, thorium and cobalt, produces dimethylformamide.

U.S. Pat. No. 2,793,211 teaches the preparation of N-alkylformamides from the corresponding alkylamine and carbon monoxide under mild temperatures using choline and the like as a catalyst.

In contrast to related art, we disclose a new preparation route to N-alkylsubstituted formamides, such as N,N-dimethylformamide or N-methylformamide, which employs only ammonia and synthesis gas as reactants (eq. 1).

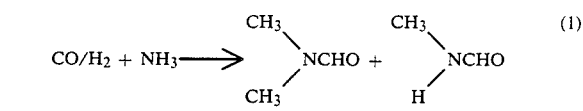

The new process of this invention allows the synthesis of N,N-dimethylformamide and N-methylformamide without the need for a methylamine, dimethylamine, trimethylamine or other alkyl-substituted amine co-reactant.

Disadvantages of the prior processes for preparing N,N-dimethylformamide and N-methylformamide include the necessity for providing certain alkylamine coreactants. It would be a significant advantage to devise a new synthetic route to dimethylformamide from the low cost building blocks ammonia and synthesis gas.

SUMMARY OF THE INVENTION

These and other desirable results are achieved by the process of this invention comprising synthesizing formamides, particularly N,N-dimethylformamide and N-methylformamide, by contacting a mixture of carbon monoxide, hydrogen and ammonia at a temperature of at least 100° C. and a pressure of 500 psig or greater with a catalyst system comprising a ruthenium-containing compound dispersed in a quaternary phosphonium salt.

DETAILED DESCRIPTION OF THE INVENTION

In the broadest aspect of this invention formamides, particularly N,N-dimethylformamide and N-methylformamide, are prepared from synthesis gas (a mixture of CO and H$_2$) and ammonia in the presence of a catalyst system comprising a ruthenium-containing compound dispersed in a quaternary phosphonium salt and heating the resultant reaction mixture to a temperature of at least 100° C. and a pressure of at least 500 psi until there is substantial formation of the desired formamide and separating said formamide products by fractional distillation from the crude liquid product under vacuum.

Carbonylation reactions used in this invention to prepare formamides, especially N,N-dimethylformamide and N-methylformamide, from synthesis gas and ammonia, can be represented by the following general equations (2) and (3):

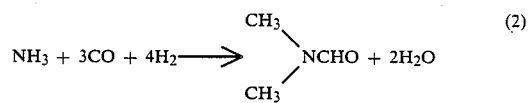

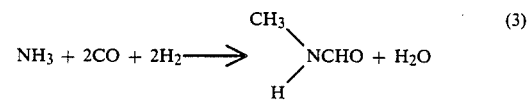

In the process of this invention the ruthenium compound is dispersed in a quaternary phosphonium salt. This process is a unique method of synthesizing N-alkylformamides from synthesis gas and ammonia. A ruthenium component is necessary in the practice of this invention in order to achieve the desired carbon monoxide plus ammonia reaction to prepare N-alkylformamides. The quaternary phosphonium salt component allows improved selectivity to the desirable formamide derivative, in accordance with the equations shown above.

In order to present the inventive concept in the greatest possible detail as to promote its understanding, the following supplementary disclosure is submitted.

The catalyst components suitable in the practice of this invention essentially include a ruthenium-containing compound dispersed in a quaternary phosphonium salt.

The actual catalytically active species is unknown but is believed to comprise ruthenium in complex combination with a quaternary phosphonium salt as well as carbon monoxide, hydrogen and ammonia.

In the practice of this invention the ruthenium-containing catalyst, as well as the quaternary salt, may be choosen from a wide variety of organic and inorganic compounds, complexes, etc., as it will be shown and illustrated. It is only necessary that the catalyst precursor actually employed contain said metal in any of its ionic states.

THe ruthenium catalyst precursors may take many different forms. For instance, the ruthenium may be added to the reaction mixture in an oxide form, as in the case of for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, for example, ruthenium(III) acetate, ruthenium naphthanate, ruthenium valerate and ruthenium complexes with carbonyl-containing ligands, such as ruthenium(III) acetylacetonate. The ruthenium may also be added to the reaction zone as a carbonyl or hydridocarbonyl derivative. Here, suitable examples include triruthenium dodecacarbonyl and other hydridocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydridocarbonyl derivatives. Among these, particularly preferred are ruthenium(IV) oxide, hydrate, ruthenium(III) chloride, ruthenium(III) acetylacetonate, and triruthenium dodecacarbonyl.

Especially good results were observed with triruthenium dodecacarbonyl.

The quaternary onium salt to be used in the catalyst composition may be any onium salt but is preferably one of those containing phosphorus, such as those of the formula:

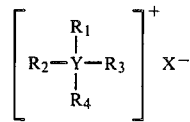

Wherein Y is phosphorus, $R_1$, $R_2$, $R_3$ and $R_4$ are organic radicals preferably alkyl, aryl or alkaryl radicals, and X is an anionic species. The organic radicals useful in this instance include those alkyl radicals having from 1 to 20 carbon atoms in a branched or linear alkyl chain, such as methyl, ethyl, n-butyl, isobutyl, octyl, 2-ethylhexyl and dodecyl radicals. Tetraethylphosphonium bromide and tetrabutylphosphonium bromide are typical examples presently in commercial production. The corresponding quaternary phosphonium acetates, nitrates, chromates, tetrafluoroborates and other halides, such as the corresponding chlorides, and iodides, are also satisfactory.

Equally useful are the phosphonium salts containing phosphorus bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to phosphorus through the aryl function.

Illustrative examples of suitable quaternary onium salts include tetra-n-butylphosphonium bromide, heptyltriphenylphosphonium bromide, tetra-n-butylphosphonium iodide, tetrabutylphosphonium acetate, tetrabutylphosphonium nitrate, tetrabutylphosphonium chromate, tetraoctylphosphonium tetrafluoroborate, tetrahexylphosphonium acetate and methyl tri-n-butylphosphonium iodide.

The preferred quaternary onium salts and bases to be used in the process comprise the tetraalkylphosphonium salts containing alkyl groups having 1 to 6 carbon atoms, such as methyl, ethyl, butyl, hexyl, heptyl and isobutyl. Tetraalkylphosphonium salts, such as the halides, bromides, chlorides and iodides, and the acetate and chromate salts are the most preferred. Good results are observed with tetra-n-butylphosphonium bromide, tetra-n-butylphosphonium iodide and heptyltriphenylphosphonium bromide. Especially good results were observed with tetrabutylphosphonium bromide.

The feedstock used in the practice of this invention comprises a synthesis gas mixture of carbon monoxide and hydrogen, plus ammonia.

The quantity of carbon monoxide, hydrogen and ammonia employed in the instant invention is not critical and may vary over a wide range. In general, however, it is desirable to conduct these synthesis in the presence of sufficient synthesis gas and ammonia to satisfy the stoichiometry of equations (1) through (3).

The relative amounts of carbon monoxide and hydrogen which can be initially present in the synthesis gas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon, and the like, or they may include gases that may, or may not undergo reaction under carbon monoxide hydrogenation conditions, such as carbon dioxide, and hydrocarbons, such as methane, ethane, propane and the like.

The quantity of ruthenium compound and quaternary phosphonium salt employed in the instant invention is not critical and may vary over a wide range. In general, the novel process is desirably conducted in the presence of a catalytically effective quantity of active ruthenium species and of the quaternary phosphonium salt which gives the desired product in reasonable yield. The reaction proceeds when employing as little as about $1 \times 10^{-4}$ weight percent and even lesser amounts, of ruthenium together with about $1 \times 10^{-6}$ weight percent or less quaternary onium salt, basis the total weight of the reaction mixture.

The upper concentration is dictated by a variety of factors including catalyst cost, partial pressure of carbon monoxide and hydrogen, operating temperature, etc. A ruthenium concentration of from about 0.0001 to about 1 weight percent in conjunction with a quaternary phosphonium concentration of from about 0.001 to about 10 weight percent, based on the total weight of the reaction mixture is desirable in the practice of this invention. The preferred ruthenium to quaternary onium catalyst atomic ratio is from about 0.005 to about 0.2. Generally, in the catalyst system, the molar ratio of the ruthenium compound to the quaternary onium salt will range from about 1:5 to about 1:200. The especially preferred molar ratio is about 1:40.

The temperature range which can usefully be employed in the process of the invention may vary over a considerable range depending upon experimental facts, including choice of catalyst, pressure and other variables. The process can take place at from 100° C. to about 300° C. or more. The preferred temperatures are above 200° and more preferably between 200° and 260° C.

Superatmospheric pressures of about 500 psi or greater lead to substantial yields of the desired amines. A preferred range is from about 3500 psi to about 7000 psi; although pressures above 9000 psi also provide useful yields of the desired products.

The pressures referred to herein represent the total pressure generated by all the reactants although they are substantially due to the carbon monoxide and hydrogen reactants.

The desired products of the reaction are formamides, especially N,N-dimethylformamide and N-methylformamide, and they are formed in significant quantities varying from about 30% to about 90% in yield. Also formed will be minor by-products, such as formamide, methylamine, and dimethylamine, as well as water. The desired formamides could be recovered from the reaction mixture by conventional means, such as fractional distillation in vacuo, etc., but distillation could be relatively difficult in some cases because of the high boiling point of the products.

The process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired formamide derivatives and said material can be recovered by methods known to the art, such as distillation, fractionation, extraction and the like. A fraction rich in the catalyst components may then be recycled to the reaction zone, if desired, and additional amine product generated.

The products have been identified in this work by one or more of the following analytical procedures; viz, gas-liquid chromatography (glc), infrared (ir), mass spectrometry, nuclear magnetic resonance (nmr) and elemental analyses, or a combination of these techniques. All temperatures are in degree centigrade and all pressures in pounds per square inch (psi).

Yields of formamide products have been estimated in accordance with equations (1) through (3), basis the quantity of hydrogen, carbon monoxide and ammonia converted, and expressed as a percentile. The figures are estimated from gas-liquid chromatography data.

The amount of each formamide derivative product has been estimated by measuring the quantity of formamide derivative formed, such as N,N-dimethylformamide or N-methylformamide, divided by the total liquid products formed.

Having described the inventive process, the following examples are submitted to supply specific and illustrative embodiments. It is to be understood the Examples are for illustrative purposes only and are not to be considered to limit the invention in any way.

Data in the attached examples illustrate the production of formamides, particularly N-methylformamide and N,N-dimethylformamide, from 1:1 $CO/H_2$ mixtures catalyzed by dispersions of ruthenium species in low melting quaternary phosphonium salts.

EXAMPLE I

In the first preparative example, formamides constitute 90.8% of the liquid product, N,N-dimethylformamide provides 44% of the formamide fraction and the liquid yield gain is 112%. The formamides are isolated from the crude liquid product by fractional distillation in vacuo.

In this example triruthenium dodecacarbonyl (0.425 g, 2.0 g atom Ru) and tetrabutylphosphonium bromide (10.0 g, 29.7 mmole) were added to an 850 ml, glass lined, pressure reactor equipped with heating and means of agitation. This mixture was flushed with nitrogen, cooled to −78° C. and 6.8 g of liquid ammonia (400 mmole) was added. The reactor was sealed, flushed with $CO/H_2$ and pressured to 136 atmospheres with $CO/H_2$ (1:1) The mixture was heated to 220° C. with rocking, and pressurized to 6300 psi with $CO/H_2$ addition from a large surge tank and the reactor held at temperature for 4 hours. Pressure was maintained at approximately 6300 psi by incremental additions of $CO/H_2$ from the surge tank.

On cooling, the reactor pressure (3600 psi) was noted, a typical gas sample taken, and the excess gas removed. The red-slurry product (22.0 g) in the glass liner was removed and analyzed by glc and Karl-Fischer titration. Typical data for the liquid product shows the presence of:

40.1% N,N-dimethylformamide
20.7% N-methylformamide
30.0% formamide
3.2% water
1.9% dimethylamine+trimethylamine The liquid yield increase is (22.0−10.4/10.4)=112%. The formamide products are recovered by fractional distillation from the crude liquid product under vacuum. The dark brown liquid residue then resolidifies upon cooling.

Analysis of the typical off-gas samples show the presence of:

47.2% hydrogen
49.4% carbon monoxide
2.5% carbon dioxide

EXAMPLES II-XI

Examples II-XI were carried out using the same process as used in Example I.

Table I illustrates the synthesis of N-methylformamide and N,N-dimethylformamide starting with a series of different ruthenium catalyst precursors (e.g. Ru₃(-

CO)₁₂, RuCl₃, RuO₂), different quaternary phosphonium salts (e.g. Bu₄PBr and Bu₄PI), various initial Ru:P:NH₃ mole ratios, operative temperatures (180°-260° C.) and pressures (4000-6300 psi).

It may be noted from an inspection of Table I that:
(a) The highest selectivity to N,N-dimethylformamide is realized in Example III.
(b) N,N-dimethylformamide is the major product fraction in Examples III and VII.
(c) N-methylformamide is the major product fraction in Examples II, IX and X.
(d) The highest total formamide production is seen in Examples VIII and XI.
(e) Formamide is the major product fraction in Examples V, VI, VIII and XI.

5. The process of claim 1 wherein the synthesis gas is composed of hydrogen and carbon monoxide in a molar ratio ranging from 1:5 to 5:1.

6. The process of claim 1 wherein the ruthenium-containing compound is selected from the group consisting of oxides of ruthenium, ruthenium salts, and ruthenium carbonyls.

7. The process of claim 6 wherein the ruthenium compound is selected from the group consisting of ruthenium(IV) oxide, hydrate, ruthenium(III) chloride, triruthenium dodecacarbonyl and ruthenium acetylacetonate.

8. The process of claim 1 wherein the preferred ruthenium-containing compound is triruthenium dodecacarbonyl.

TABLE I

SYNTHESIS OF FORMAMIDES FROM SYNGAS/AMMONIA

| | | | Mole Ratio | Operating | | Liquid Product Composition[a] | | | | | Liquid |
|---|---|---|---|---|---|---|---|---|---|---|---|
| Example | Ruthenium Species | Reaction Media | Ru:P:NH₃ | Temp (°C.) | Pres (psi) | DMF | NMF | H₂NCO | Me₃N + Me₂NH | H₂O | Yield(%) |
| II | Ru₃(CO)₁₂ | Bu₄PI | 2  26  400 | 220 | 6300 | 23.9 | 42.7 | | | 18.3 | 112 |
| III | RuCl₃ | Bu₄PBr | 2  30  400 | 220 | 6300 | 40.3 | 20.6 | 32.9 | 3.5 | 2.5 | 83 |
| IV | RuO₂ | Bu₄PBr | 4  30  400 | 220 | 6300 | 15.2 | 0.1 | 1.0 | 47.2 | 5.4 | 72 |
| V | Ru₃(CO)₁₂ | Bu₄PBr | 2  30  800 | 220 | 6300 | 10.7 | 21.5 | 49.7 | | 2.7 | 103 |
| VI | Ru₃(CO)₁₂ | Bu₄PBr | 1  15  800 | 220 | 6300 | 10.8 | 20.9 | 47.9 | | 4.0 | 115 |
| VII | Ru₃(CO)₁₂ | Bu₄PBr | 1  15  800 | 260 | 6300 | 20.7 | 9.7 | 2.1 | 15.0 | 5.3 | 208 |
| VIII | Ru₃(CO)₁₂ | Bu₄PBr | 1  15  800 | 180 | 6300 | 1.0 | 4.3 | 78.9 | | 0.8 | 256 |
| IX | Ru₃(CO)₁₂ | Bu₄PBr | 2  15  800 | 220 | 6300 | 19.3 | 26.0 | 15.8 | 7.6 | 3.3 | 117 |
| X | Ru₃(CO)₁₂ | Bu₄PBr | 1  15  800 | 260 | 4000 | 22.9 | 29.4 | 1.4 | | 3.4 | 87 |
| XI | Ru₃(CO)₁₂ | Bu₄PBr | 1  15  800 | 180 | 4000 | 0.7 | 4.1 | 80.8 | | 0.7 | 183 |

[a]DMF, N,N—dimethylformamide, NMF, N—methylformamide.

What is claimed is:

1. A process for synthesizing formamide, N,N-dimethylformamide and N-methylformamide, which comprises contacting a mixture of carbon monoxide, hydrogen and ammonia at a pressure of 500 psi or greater and at a temperature of 100° C. or greater with a catalyst system comprising a mixture of a ruthemium-containing compound and a quaternary phosphonium salt.

2. The process of claim 1 wherein the mixture is under a pressure of 500 psi to 9000 psi.

3. The process of claim 1 wherein the mixture is under a pressure of 3500 psi to 7000 psi.

4. The process of claim 1 wherein the temperature is 100° C. to 300° C.

9. The process of claim 1 wherein the quaternary phosphonium salt is a tetraalkylphosphonium salt.

10. The process of claim 9 wherein said alkyl groups contain 1-9 carbon atoms.

11. The process of claim 1 wherein the quaternary phosphonium salt is a mixed alkaryl phosphonium quaternary salt.

12. The process of claim 10 wherein the quaternary phosphonium salt is selected from the group consisting of tetra-n-butylphosphonium bromide, and tetra-n-butylphosphonium iodide.

13. The process of claim 11 wherein the mixed alkaryl phosphonium quaternary is heptyltriphenylphosphonium bromide.

* * * * *